(12) United States Patent
Tokunaga et al.

(10) Patent No.: US 8,318,139 B2
(45) Date of Patent: Nov. 27, 2012

(54) COMPOSITION FOR ORAL CAVITY

(75) Inventors: Tadayuki Tokunaga, Tokyo (JP); Kazushi Oshino, Tokyo (JP)

(73) Assignee: Kao Corporation, Tokyo (JP)

( * ) Notice: Subject to any disclaimer, the term of this patent is extended or adjusted under 35 U.S.C. 154(b) by 923 days.

(21) Appl. No.: 10/584,142

(22) PCT Filed: Dec. 24, 2004

(86) PCT No.: PCT/JP2004/019407
§ 371 (c)(1), (2), (4) Date: Jun. 26, 2006

(87) PCT Pub. No.: WO2005/063183
PCT Pub. Date: Jul. 14, 2005

(65) Prior Publication Data
US 2007/0128131 A1 Jun. 7, 2007

(30) Foreign Application Priority Data

Dec. 26, 2003 (JP) ................................. 2003-434725

(51) Int. Cl.
*A61K 8/21* (2006.01)
(52) U.S. Cl. ......................................................... 424/52
(58) Field of Classification Search .................. None
See application file for complete search history.

(56) References Cited

U.S. PATENT DOCUMENTS

| | | | |
|---|---|---|---|
| 4,193,988 A * | 3/1980 | Forward et al. | 424/52 |
| 5,037,636 A | 8/1991 | Chan | |
| 6,036,944 A * | 3/2000 | Winston et al. | 424/49 |
| 6,214,321 B1 * | 4/2001 | Lee et al. | 424/52 |
| 6,372,198 B1 * | 4/2002 | Abbate | 424/49 |
| 6,471,946 B1 * | 10/2002 | Takatsuka et al. | 424/52 |
| 7,300,645 B2 * | 11/2007 | Takatsuka et al. | 424/52 |
| 2006/0134019 A1 | 6/2006 | Oshino et al. | |

FOREIGN PATENT DOCUMENTS

| | | |
|---|---|---|
| JP | 57-42519 | 3/1982 |
| JP | 58-15015 | 1/1983 |
| JP | 58-35163 | 8/1983 |
| JP | 3-151319 | 6/1991 |
| JP | 09-143043 | 6/1997 |
| JP | 2000-191486 | 7/2000 |
| JP | 2002-104948 | 4/2002 |
| JP | 2002-167318 | 6/2002 |
| JP | 2003-226627 | 8/2003 |

* cited by examiner

*Primary Examiner* — Frederick Krass
*Assistant Examiner* — Snigdha Maewall
(74) *Attorney, Agent, or Firm* — Oblon, Spivak, McClelland, Maier & Neustadt, L.L.P.

(57) ABSTRACT

There is provided a composition for oral cavity containing a monofluorophosphoric acid, which can supply calcium ions in a stable manner. The composition comprises (A) a calcium ion-supplying compound which supplies calcium ions at 100 to 16000 ppm, (B) a monofluorophosphate ion-supplying compound which supplies monofluorophosphate ions at 250 to 25000 ppm, and (C) one or more acids selected from the group consisting of lactic acid, malic acid, and tartaric acid, and the composition has a pH of 4 to 6.2.

26 Claims, No Drawings

COMPOSITION FOR ORAL CAVITY

FIELD OF THE INVENTION

The present invention relates to a composition for oral cavity containing a monofluorophosphate.

BACKGROUND OF THE INVENTION

The enamel of the teeth contains hydroxyapatite as a main component. In the oral cavity, elution of phosphate and calcium ions (decalcification) and crystallization into calcium phosphate and hydroxyapatite (remineralization) are normally at equilibrium. Fluoride ions are capable of preventing dental caries by suppressing decalcification in an acidic environment, and by facilitating crystallization of calcium and phosphate ions in a neutral environment, i.e. remineralization.

However, in the case where fluoride and calcium ions are contained in the composition in advance, such a case leads to precipitation of calcium fluoride in the composition and enlargement of the particle size thereof, so that absorption of calcium fluoride into the teeth becomes almost impossible. Accordingly, if there is a need for incorporating a calcium ion-supplying compound or an abrasive containing calcium in a composition, it is preferred to use in the composition a monofluorophosphate salt which has little interactions with calcium ions, because it can be decomposed into fluoride and phosphate ions in the oral cavity.

However, even when a monofluorophosphate salt is used, an interactive reaction occurs inevitably over time insofar as a water-soluble calcium salt coexists therewith, so that the use of a monofluorophosphate salt is still insufficient. To improve such a problem, there are known methods, for example, a method of formulating sodium pyrophosphate or polyphosphate salt (JP-A-S58-35163), a method of formulating trimagnesium phosphate (JP-A-S62-35963; Japanese Patent Publication No. 1-23404), a method of formulating zinc tripolyphosphate (JP-A-H07-544), a method of allowing soluble phosphate salt to coexist (JP-A-2003-226627). Yet there has been a problem that phosphate ions have a calcium-chelating effect and therefore the calcium ion concentration responsible for remineralization of the teeth is decreased.

Patent Document 1: JP-A-S58-35163
Patent Document 2: JP-A-S62-35963
Patent Document 3: JP-A-H01-23404
Patent Document 4: JP-A-H07-544
Patent Document 5: JP-A-2003-226627

The present invention provides a composition for oral cavity containing:
(A) a calcium ion-supplying compound which supplies calcium ions at 100 to 16000 ppm;
(B) a monofluorophosphate ion-supplying compound which supplies monofluorophosphate ions at 250 to 25000 ppm; and
(C) one or more acids selected from the group consisting of lactic acid, malic acid, and tartaric acid, and the composition has a pH of 4 to 6.2.

MODE FOR CARRYING OUT THE INVENTION

The present inventors have found that even when monofluorophosphate and calcium ions coexist, an interactive reaction can be suppressed by adjusting the pH to 4 to 6.2 using a particular acid, thereby enabling calcium ions necessary for remineralization to be stably supplied to the teeth.

The present invention provides a composition for oral cavity containing a monofluorophosphate salt that allows for the stable supply of calcium ions. By using the composition for oral cavity of the present invention, calcium ions can be stably supplied to the teeth. This facilitates remineralization of the teeth, and is effective for the prevention of dental caries.

Examples of the calcium ion-supplying compound (A) used in the composition for oral cavity of the present invention include calcium glycerophosphate, calcium glucose-1-phosphate, calcium glucose-6-phosphate, phosphorylated oligosaccharide calcium, calcium hydroxide, calcium chloride, calcium acetate, calcium formate, calcium lactate, calcium nitrate, calcium gluconate, calcium benzoate, calcium isobutyrate, calcium propionate, calcium salicylate, and mixtures thereof.

Among these calcium ion-supplying compounds, calcium lactate and calcium glycerophosphate etc. are preferred in view of palatability.

In view of efficiently producing calcium fluoride within the oral cavity, it is preferred that the calcium ion-supplying compound in the composition for oral cavity contain a calcium ion-supplying compound which supplies calcium ions at 100 to 16000 ppm, more preferably at 100 to 8000 ppm, more preferably at 200 to 4000 ppm, even more preferably a calcium ion-supplying compound which supplies calcium ions at 400 to 4000 ppm. To achieve a calcium ion concentration of 100 ppm or more, it is necessary to use a calcium ion-supplying compound that dissolves at this concentration or more in the composition for oral cavity.

Meanwhile, it is preferred not to substantially add a chelating agent to prevent the decrease of calcium ion concentration given to the remineralization of the teeth. Examples of chelating agents include pyrophosphate salt, polyphosphate salt, EDTA, citrate, and orthophosphate salt. The chelating agent is preferably 0.1% by weight or less, more preferably 0.01% by weight or less in the composition for oral cavity.

Examples of the monofluorophosphate ion-supplying compound (B) used in the composition for oral cavity of the present invention include sodium monofluorophosphate, potassium monofluorophosphate, magnesium monofluorophosphate, and calcium monofluorophosphate. Sodium monofluorophosphate is preferred. Monofluorophosphate ions remain in the oral cavity, especially in for example dental plaque, degraded over time by for example phosphatase in saliva and dental plaque, and continuously supply fluoride ions to the teeth. The monofluorophosphate ion-supplying compound in the composition for oral cavity preferably contains a monofluorophosphate ion-supplying compound which supplies monofluorophosphate ions at 250 to 25000 ppm, more preferably at 2500 to 10000 ppm, even more preferably contains a monofluorophosphate ion-supplying compound which supplies monofluorophosphate ions at 4000 to 9000 ppm.

The composition for oral cavity of the present invention is characterized in that the pH is adjusted to 4 to 6.2 by (C) an acid. By adjusting the pH to 6.2 or less, more preferably to 6 or less, degradation of the monofluorophosphoric acid is efficiently suppressed. In addition, in view of astringency upon use and prevention of discoloration of the composition for oral cavity, a pH of 4.0 or more is preferred, more preferably 4.5 or more, more preferably 5 or more, even more preferably 5.2 or more. In addition, in view of its a stringency possibly further enhanced by an acidic environment, an aluminum ion preferably should not be substantially contained in the composition for oral cavity of the present invention. It is preferred that aluminum ions are 0.1% by weight or less, more preferably 0.01% by weight or less in the composition for oral cavity.

The content of the acid (C) in the composition for oral cavity is preferably 0.05 to 10% by weight of the total composition, more preferably 0.1 to 5% by weight, even more preferably 1 to 3% by weight. In addition, when the composition for oral cavity of the present invention does not contain a salt of the acid (C), the value of acid ions quantified by the calibration curve method using ion chromatography is considered the content of the acid (C). For example, the content of malic acid can be measured using DX-320 from Dionex (equipped with EG-40) as the ion chromatography device, and with the following measurement conditions: separation column: IonPac AS-16; guard column: IonPac AG-16; eluent: KOH (using EG-40); flow rate: 1.0 mL/min; gradient: 10 to 70 mmol/L (0 to 25 min); suppressor: ASRS (200 mA); and detector: electric conductivity detector. The content of lactic acid can be measured using DX-320 from Dionex (equipped with EG-40) as the ion chromatography device, and with the following measurement conditions: separation column: IonPac AS-9HC; guard column: IonPac AG-9HC; eluent: KOH (using EG-40); flow rate: 11.0 mL/min; gradient: 5 to 70 mmol/L (30 min); suppressor: ASRS (200 mA); and detector: electric conductivity detector (dilution and filtration steps are carried out as necessary).

The acid (C) used in the composition for oral cavity of the present invention is one or more acids selected from the group consisting of lactic acid, malic acid, and tartaric acid. Further, in view of increasing the activity of calcium ions, lactic acid and malic acid are preferred, and more preferably malic acid.

In addition, it is preferred to further add a salt of the acid (C) into the composition for oral cavity of the present invention. This is because a buffer action is shown at a pH of 4 to 6.2, and stability is increased. Examples of salts of the acid (C) include a sodium salt, potassium salt, arginine salt, and ammonium salt. Alkali metal salts such as sodium and potassium salts are preferred. The salt of the acid (C) may be directly added when preparing the composition for oral cavity of the present invention, or the acid (C) and an alkali such as sodium hydroxide and potassium hydroxide may be separately added, and a buffer system of the acid and a salt thereof may be formed in the composition. The total content of the acid (C) and a salt thereof in the composition for oral cavity is preferably 0.05 to 10% by weight of the total composition, more preferably 0.1 to 5% by weight, even more preferably 1 to 3% by weight. In addition, when the composition for oral cavity of the present invention contains the acid and a salt thereof, the amount of acid ions measured by the above-mentioned ion chromatography using the calibration curve method is considered the total content of the acid (C) and the salt thereof in the composition for oral cavity.

Further, the pH of the composition of the present invention can be directly measured if it is a liquid composition such as a mouthwash, but is measured as an aqueous solution of 10% by weight in the case of e.g. toothpaste.

Moreover, it is preferred to further add sugar alcohol in the composition for oral cavity of the present invention. Examples of the sugar alcohol to be added include lactitol, isomaltitol, maltotriitol, isomaltotriitol, panitol, isomaltotetraitol, erythritol, arabitol, ribitol, xylitol, sorbitol, mannitol, and maltitol. The content of the sugar alcohol in the composition is preferably 20 to 70% by weight, more preferably 30 to 60% by weight, even more preferably 40 to 50% by weight.

In addition, if the composition for oral cavity of the present invention is a toothpaste, viscosity at 25° C. is preferably 1500 to 10000 dPa·s, more preferably 2000 to 7000 dPa·s. The viscosity can be measured using the measuring equipment viscometer DVR-B2 with Helipath (from TOKI SANGYO CO., LTD.) and measuring rotor Rotor C, and with conditions of a measuring time of 60 seconds and a measuring temperature of 25° C.

In the present invention, an anionic surfactant generally used in a composition for oral cavity, for example an alkyl sulfate such as sodium lauryl sulfate and N-acylamino acid salt such as N-acylsarcosinate salt, may be contained in an amount that does not impair the effect of the present invention.

In addition, an abrasive such as silicic anhydride, dibasic calcium phosphate, and calcium carbonate; a humectant such as glycerin and polyethylene glycol; a foaming agent; a binder such as sodium carboxymethylcellulose and carageenan; a sweetening agent such as sodium saccharin; a colorant; a preservative such as methyl paraoxybenzoate; a bactericide such as benzethonium chloride, triclosan, and isopropylmethylphenol; an anti-inflammatory agent such as β-glycyrrhetinic acid and tocopherol; and a flavorant etc. commonly used in a composition for oral cavity can be added to the composition for oral cavity of the present invention.

The composition for oral cavity of the present invention can be used as, for example, a tooth powder, wet toothpaste, toothpaste, liquid toothpaste, or mouthwash.

EXAMPLES

Examples 1 and 2 Mouthwash (1) Preparation of Mouthwash

The mouthwashes of Examples 1 and 2 and Comparative Example 1 as shown in Table 1 were prepared.

(2) Method of Measurement a. Stability in Storage

The mouthwashes as shown in Table 1 were stored at 40° C. for 2 weeks, at the end of which the following evaluations were carried out.

1. Changes in Appearance

The conditions after storage were visually observed and evaluated by the following criteria.

2 points: There is no settling or precipitation of crystals and the product is transparent.

1 point: There is no settling or precipitation of crystals, but clouding is seen in the product.

0 point: Settling and precipitation of crystals are seen.

2. Residual Factor of Calcium and Monofluorophosphate Ions

Calcium and monofluorophosphate ions contained in the liquid before and after storage were measured, and the residual factors of each ion were calculated from the values before and after storage.

The quantification of the residual amount of Ca ions was carried out by adding 0.5 mL of mouthwash so that 12 mol/L hydrochloric acid was 4 W/V %, and filled up to 100 mL (200-fold dilution) as a measurement sample. An ICP spectrometry analyzer from Horiba, Ltd. (JY288U) was used with emission line of Ca; 317.933 nm, and quantification was carried out by calibration curve method (range of calibration: 2 to 20 ppm).

The quantification of monofluorophosphate ions was carried out by ion chromatography using calibration curve method. The ion chromatography device used was DX-320 from Dionex (equipped with EG-40), and the measurement conditions used were as follows: separation column: IonPac AS-16; guard column: IonPac AG-16; eluent: KOH (using EG-40); flow rate: 1.0 mL/min; gradient: 10 to 70 mmol/L (0 to 20 min), suppressor: ASRS (200 mA), and detector: electric conductivity detector.

b. Usability (Astringency)

Evaluations by 10 test subjects (5 male, 5 female) were carried out by taking up the mouthwashes as shown in Table 2 into the mouth and spitting it out after gargling. The usability was evaluated by the following criteria by the test subject, and the mean value was calculated.

2 points: It can be used without problems.
1 point: There is slight astringency, but it is bearable for use.
0 point: Astringency is strong, and it is unbearable for use.

The results are shown in Table 1. The contents of components shown in Tables 1 and 2 are % by weight.

Examples 1 and 2, which are the mouthwashes of the present invention, showed superior stability in storage as compared to the composition of Comparative Example 1. In particular, Example 2 showed a high residual factor of both monofluorophosphate and calcium ions even in comparison with Example 1.

TABLE 1

|  |  | Example 1 | Example 2 | Comparative Example 1 |
|---|---|---|---|---|
| Composition | Calcium glycerophosphate | 1 | 1 | 1 |
|  | Sodium monofluorophosphate | 0.7 | 0.7 | 0.7 |
|  | Lactic acid | 0.6 | 2 |  |
|  | Sodium hydroxide (pH regulator) |  | 0.91 |  |
|  | Purified water | Balance | Balance | Balance |
|  | Total | 100 | 100 | 100 |
| pH immediately after formulation |  | 5 | 5 | 8 |
| Usability (Astringency) |  | 1.6 | 1.5 | 1.5 |
| Stability in storage | Changes in appearance | 2 | 2 | 0 |
|  | Residual factor of monofluorophosphate ions | 87% | 99% | 30% |
|  | Residual factor of calcium ions | 88% | 94% | 32% |

Examples 3 to 7 Toothpaste (1) Preparation of Toothpaste

The toothpastes of Examples 3 to 7 and Comparative Examples 2 and 3 as shown in Table 2 were prepared. The viscosity at 1 day post preparation was approximately 2500 dPa·s for all toothpastes (the above-mentioned measurement conditions).

(2) Method of Measurement a. Stability in Storage

The test toothpastes as shown in Table 2 were stored at 50° C. for 1 month, at the end of which the following evaluations were carried out. In other words, the residual factor of calcium ions and discoloration of toothpaste were used as indicators of the stability in storage of the toothpastes.

1. Residual Factor of Calcium Ions

The residual factor of calcium ions was calculated from the values of quantification of the calcium ions before and after storage (0 week, 2 weeks, 1 month).

The quantification of calcium ions was carried out by a chelate color-forming method.

The quantification by the chelate color-forming method was carried out using Calcium C-Test Wako from Wako Pure Chemical Industries, Ltd. The calcium in the sample binds to OCPC (orthocresol phthalein complexone) under alkaline conditions and gives a violet-red color. The absorbency of this violet-red color was measured, and quantified by the calibration curve method.

2. Changes from Discoloration

Discoloration status of the toothpastes were visually observed after storage (after 2 weeks), and evaluated by the following criteria.

2 points: There was no change as compared to before storage.
1 point: Slight change in color was seen, but it is within the permissible range.
0 point: The change in color is apparent.

b. Usability (Astringency)

Approximately 1 g of test toothpaste as shown in Table 2 was taken up onto a toothbrush, used to brush freely, and spitted out after gargling. Evaluation from such use was carried out by 10 test subjects (5 male, 5 female) using the following criteria (evaluation was done by each test subject). The mean value was calculated.

2 points: It can be used without problems.
1 point: Slight astringency was felt, but it is bearable for use.
0 point: Astringency is strong, and it is unbearable for use.

The results are shown in Table 2.

Examples 3 to 7, which are the toothpastes of the present invention, showed superior stability in storage as compared to the composition of Comparative Example 3. Further, Comparative Example 2 showed high residual factor of calcium ions, but apparent discoloration of toothpaste occurred and there was also a problem in usability. Moreover, Example 4 was bearable in use but astringency was felt.

TABLE 2

|  |  | Example | | | | | Comparative Example | |
|---|---|---|---|---|---|---|---|---|
|  |  | 3 | 4 | 5 | 6 | 7 | 2 | 3 |
| Composition | Calcium Glycerophosphate | 1 | 0.6 | 0.6 |  | 0.6 | 0.6 | 0.6 |
|  | Calcium Lactate |  | 0.6 | 0.6 | 1.5 | 0.6 | 0.6 | 0.6 |
|  | Sodium Monofluorophosphate | 0.7 | 0.7 | 0.7 | 0.7 | 0.7 | 0.7 | 0.7 |
|  | Lactic Acid | 2 | 2 | 0.2 | 2 |  | 2 |  |
|  | Malic Acid |  |  |  |  | 0.17 |  |  |
|  | Sodium Hydroxide (pH Regulator) | 1.2 | 0.36 |  | 0.9 |  |  |  |
|  | Sorbit Solution (70% by weight) | 40 | 40 | 40 | 40 | 40 | 40 | 40 |
|  | Xylitol | 6 | 6 | 6 | 6 | 6 | 6 | 6 |
|  | Silicic Anhydride | 15 | 15 | 15 | 15 | 15 | 15 | 15 |
|  | Sodium Saccharin | 0.1 | 0.1 | 0.1 | 0.1 | 0.1 | 0.1 | 0.1 |
|  | Sodium lauryl sulfate | 1.2 | 1.2 | 1.2 | 1.2 | 1.2 | 1.2 | 1.2 |

TABLE 2-continued

|  |  | Example | | | | | Comparative Example | |
|---|---|---|---|---|---|---|---|---|
|  |  | 3 | 4 | 5 | 6 | 7 | 2 | 3 |
|  | Sodium Carboxymethylcellulose | 1 | 1 | 1 | 1 | 1 | 1 | 1 |
|  | Carageenan | 0.2 | 0.2 | 0.2 | 0.2 | 0.2 | 0.2 | 0.2 |
|  | Xanthan Gum | 0.2 | 0.2 | 0.2 | 0.2 | 0.2 | 0.2 | 0.2 |
|  | Polyethylene Glycol 600 | 4 | 4 | 4 | 4 | 4 | 4 | 4 |
|  | Flavorant (Peppermint) | 1 | 1 | 1 | 1 | 1 | 1 | 1 |
|  | Purified Water | Balance | Balance | Balance | Balance | Balance | Balance | Balance |
|  | Total | 100 | 100 | 100 | 100 | 100 | 100 | 100 |
| pH (Aqueous Solution of 10% by Weight) | | 6 | 4 | 6 | 5 | 6 | 3.5 | 7.5 |
| Stability in Storage | Changes from Discoloration | 2 | 2 | 2 | 2 | 2 | 0 | 2 |
|  | Residual Factor of Calcium Ions*[1] | 99% | 99% | 97% | 99% | 97% | 99% | 55% |
|  | Residual Factor of Calcium Ions*[2] | — | 95% | 76% | — | 80% | 99% | 39% |
| Usability (Astringency) | | 1.8 | 1.2 | 1.9 | 1.9 | 1.9 | 0.3 | 1.9 |

*[1] 14 days
*[2] 1 month

The invention claimed is:

1. A homogeneous composition for an oral cavity comprising:
   (A) a calcium ion-supplying compound which supplies calcium ions at 100 to 16000 ppm;
   (B) a monofluorophosphate ion-supplying compound which supplies monofluorophosphate ions at 250 to 25000 ppm; and
   (C) one or more acids selected from the group consisting of lactic acid, malic acid, and tartaric acid,
   wherein the composition has a pH of from 4 to 6.2; and
   wherein the composition comprises a total amount of chelating agents selected from the group consisting of pyrophosphate salts, polyphosphate salts, EDTA, citrates and orthophosphate salts, of 0.1% by weight or less based on the total weight of the composition; and
   wherein the acid (C) is present in an amount of from 0.17 to 3% by weight.

2. The composition for an oral cavity according to claim 1, wherein the composition comprises the acid component (C) as an acid and a salt of the acid.

3. The composition for an oral cavity according to claim 1 or 2, further comprising a sugar alcohol.

4. A process of stabilizing a composition for an oral cavity comprising (A) a calcium ion-supplying compound which supplies calcium ions at 100 to 16000 ppm and (B) a monofluorophosphate ion-supplying compound which supplies monofluorophosphate ions at 250 to 25000 ppm, characterized in that the process comprises adding (C) one or more acids selected from the group consisting of lactic acid, malic acid, and tartaric acid to the composition to adjust the pH to from 4 to 6.2 wherein the composition comprises a total amount of chelating agents selected from the group consisting of pyrophosphate salts, polyphosphate salts, EDTA, citrates and orthophosphate salts, of 0.1% by weight or less based on the total weight of the composition; and
   wherein the acid (C) is present in an amount of from 0.17 to 3% by weight.

5. A homogeneous composition for an oral cavity, comprising:
   (A) a calcium ion-supplying compound which supplies calcium ions at 100 to 16,000 ppm;
   (B) a monofluorophosphate ion-supplying compound which supplies monofluorophosphate ions at 250 to 25,000 ppm; and
   (C) one or more acids selected from the group consisting of lactic acid, malic acid, and tartaric acid,
   wherein the composition has a pH of from 4 to 6.2;
   wherein the composition meets at least one of the following requirements:
      (i) does not settle and does not precipitate crystals after storage at 40° C. for two weeks, and
      (ii) has a residual factor of calcium ions of 76% or more after storage at 50° C. for one month; and
   wherein the composition comprises a total amount of chelating agents selected from the group consisting of pyrophosphate salts, polyphosphate salts, EDTA, citrates and orthophosphate salts of 0.1% by weight or less based on the total weight of the composition; and
   wherein the acid (C) is present in an amount of from 0.17 to 3% by weight.

6. The composition according to claim 1, wherein the calcium ion-supplying compound is at least one selected from the group consisting of calcium glycerophosphate, calcium glucose-1-phosphate, calcium glucose-6-phosphate, phosphorylated oligosaccharide calcium, calcium hydroxide, calcium chloride, calcium acetate, calcium formate, calcium lactate, calcium nitrate, calcium gluconate, calcium benzoate, calcium isobutyrate, calcium propionate, and calcium salicylate.

7. The composition according to claim 1, wherein the monofluorophosphate ion-supplying compound is at least one selected from the group consisting of sodium monofluorophosphate, potassium monofluorophosphate, magnesium monofluorophosphate and calcium monofluorophosphate.

8. The composition according to claim 1, having a pH of 5.2 to 6.2.

9. The composition according to claim 1, wherein the content of the acid (C) is 1 to 3% by weight based on the total weight of the composition.

10. The composition according to claim 1, comprising 0.01% by weight or less of chelating agents based on the total weight of the composition.

11. A toothpaste comprising the composition according to claim 1, further comprising xylitol, sodium lauryl sulfate, and silicic anhydride;
   wherein the calcium ion-supplying compound (A) is calcium glycerophosphate, the monofluorophosphate ion-supplying compound (B) is sodium monofluorophosphate, and the acid (C) is lactic acid;
   wherein the composition has a residual factor of calcium ions of 76-95% after storage at 50° C. for one month; and
   wherein the pH is 4-6.

12. A mouthwash comprising the composition according to claim 1, further comprising water;
   wherein the calcium ion-supplying compound (A) is calcium glycerophosphate, the monofluorophosphate ion-supplying compound (B) is sodium monofluorophosphate, the acid (C) is lactic acid;
   wherein the composition is transparent, does not settle and does not precipitate crystals after storage at 40° C. for two weeks.

13. The composition according to claim 1, comprising 0.01% by weight or less of aluminum based on the total weight of the composition.

14. The composition according to claim 1, wherein the composition meets at least one of the following requirements:
   (i) the composition is transparent, does not settle and does not precipitate crystals after storage at 40° C. for two weeks, and
   (ii) has a residual factor of calcium ions of 76% or more after storage at 50° C. for one month.

15. The composition according to claim 5, which is in the form of a solution and does not settle and does not precipitate crystals after storage at 40° C. for two weeks.

16. The composition according to claim 5, which is in the form of a paste or gel and has a residual factor of calcium ions of 76% or more after storage at 50° C. for one month.

17. The composition according to claim 5, which is in the form of a paste or gel and has a residual factor of calcium ions of 76-95% after storage at 50° C. for one month.

18. The composition according to claim 1, which substantially does not include a phosphate ion-supplying compound.

19. The composition according to claim 5, which substantially does not include a phosphate ion-supplying compound.

20. The composition according to claim 1 having a pH of from 4 to less than 6.

21. The composition according to claim 5 having a pH of from 4 to less than 6.

22. The composition according to claim 1, wherein the calcium ion-supplying compound (A) supplies calcium ions at 400 to 16000 ppm; and
   wherein the amount of the calcium ion-supplying compound is greater than the amount of the monofluorophosphate ion-supplying compound.

23. The composition according to claim 5, wherein the calcium ion-supplying compound (A) supplies calcium ions at 400 to 16000 ppm; and
   wherein the amount of the calcium ion-supplying compound is greater than the amount of the monofluorophosphate ion-supplying compound.

24. The composition according to claim 1, wherein the monofluorophosphate ion-supplying compound and the calcium ion-supplying compound are present in a weight ratio of 0.7:1 to 0.46:1.

25. The composition according to claim 5, wherein the monofluorophosphate ion-supplying compound and the calcium ion-supplying compound are present in a weight ratio of 0.7:1 to 0.46:1.

26. A homogeneous composition for an oral cavity comprising:
   (A) a calcium ion-supplying compound which supplies calcium ions at 100 to 16000 ppm;
   (B) a monofluorophosphate ion-supplying compound which supplies monofluorophosphate ions at 250 to 25000 ppm; and
   (C) one or more acids selected from the group consisting of lactic acid, malic acid, and tartaric acid,
   wherein the composition has a pH of from 4 to 6.2; and
   wherein the composition comprises substantially no chelating agents selected from the group consisting of pyrophosphate salts, polyphosphate salts, EDTA, citrates and orthophosphate salts; and
   wherein the acid (C) is present in an amount of from 0.17 to 3% by weight.

* * * * *